US00PP21426P3

(12) United States Plant Patent
Matsui

(10) Patent No.: US PP21,426 P3
(45) Date of Patent: Oct. 26, 2010

(54) *ZOYSIAGRASS* PLANT 'TMX'
(50) Latin Name: *Zoysia matrella*
Varietal Denomination: TMX

(75) Inventor: Kunio Matsui, Nishikamo-gun (JP)
(73) Assignee: Toyota Jidosha Kabushiki Kaisha, Tokyo (JP)

( * ) Notice: Subject to any disclaimer, the term of this patent is extended or adjusted under 35 U.S.C. 154(b) by 175 days.
(21) Appl. No.: 12/149,800
(22) Filed: May 8, 2008
(65) Prior Publication Data
US 2008/0282436 P1 Nov. 13, 2008
(30) Foreign Application Priority Data
May 8, 2007 (JP) ..... 21038
(51) Int. Cl.
*A01H 5/00* (2006.01)
(52) U.S. Cl. ..... Plt./390
(58) Field of Classification Search ..... Plt./390
See application file for complete search history.

(56) References Cited

U.S. PATENT DOCUMENTS

PP17,514 P3 3/2007 Matsui

*Primary Examiner*—Kent L Bell
(74) *Attorney, Agent, or Firm*—Oblon, Spivak, McClelland, Maier & Neustadt, L.L.P.

(57) ABSTRACT

The present culivar 'TMX' (*Zoysia matrella* Merr.) advantageously has a very slow growing rate in terms of plant height as compared with existing cultivars and requires mowing not more than once a year so as to be maintained in fair condition and allows the amount of fertilizer to be reduced. It also has a high-level of shade tolerance.

8 Drawing Sheets

Latin name of the genus and species of the plant claimed: The present invention relates to the species *Zoysia matrella* Merr.

Variety denomination: 'TMX'.

BACKGROUND OF THE INVENTION

Field of Invention

The present invention relates to a new and distinct perennial variety of *Zoysiagrass* asexually reproduced and selected.

SUMMARY OF THE INVENTION

The present invention relates to a new and distinct Zoysiagrass cultivar (*Zoysia matrella* Merr.) named 'TMX'.

*Zoysiagrass* is a popular lawn grass which has been widely used as greening turf. The turf thereof, however, should be mowed 3 to 5 times per year so as to be maintained in beautiful condition. Since the newly developed 'TMX' advantageously has a very slow growing rate in terms of plant height as compared with conventional cultivars, mowing is required not more than once a year to maintain fair condition and the amount of fertilizer can be reduced to almost less than half. Therefore, labors and cost necessary for maintenance of the turf as well as clipping from lawn-mowing can be reduced. Furthermore, the cultivar can be readily grown in a place where a lawnmower cannot be conveniently used, such as on a rooftop of a building. In addition, 'TMX' has superior shade tolerance to that of a conventional cultivar, and thus can be raised even in a place with insufficient sunlight exposure.

In addition, it is expected that prevalence of 'TMX' facilitates greening of the rooftop and schoolyard and leads to alleviation of heat island phenomenon and reduction of the amount of $CO_2$.

For purposes of registration under the "International Convention for the Protection of New Varieties of Plants" (generally known by its French acronym as the UPOV Convention) and noting sections 1612 of the Manual of Patent Examining Procedure, it is proposed that the new variety of *Zoysiagrass* of the present invention be named 'TMX'.

BRIEF DESCRIPTIONS OF THE ILLUSTRATIONS

FIG. 1 is a set of photographs comparing spikestems of control cultivars and the present cultivar ('TMX') (Left: Emerald; Middle: TM9; Right: 'TMX'). Photographed on May 22, 2006 in Nishikamo-gun, Aichi, Japan.

FIG. 2 is a set of photographs comparing grass shapes of control cultivars and the present cultivar ('TMX') (Upper: Emerald; Middle: TM9; Lower: 'TMX'). Photographed on May 12, 2006 in Nishikamo-gun, Aichi, Japan.

FIG. 3 is a set of photographs comparing stolons of control cultivars and the present cultivar ('TMX') (Upper: Emerald; Middle: TM9; Lower: 'TMX'). Photographed on Oct. 20, 2005 in Nishikamo-gun, Aichi, Japan.

FIG. 4 is a photograph showing a full view of test field for the present cultivar ('TMX') ((1): Individually planted plot of Emerald; (2): Individually planted plot of TM9; (3); Individually planted plot of 'TMX'). Photographed on Sep. 25, 2006 in Nishikamo-gun, Aichi, Japan.

FIG. 5 is a set of photographs comparing control cultivars and the present cultivar ('TMX') in terms of plant vigor in fall (Upper: Emerald; Middle: TM9; Lower: 'TMX'). Photographed on Nov. 13, 2006 in Nishikamo-gun, Aichi, Japan.

Figure 8:
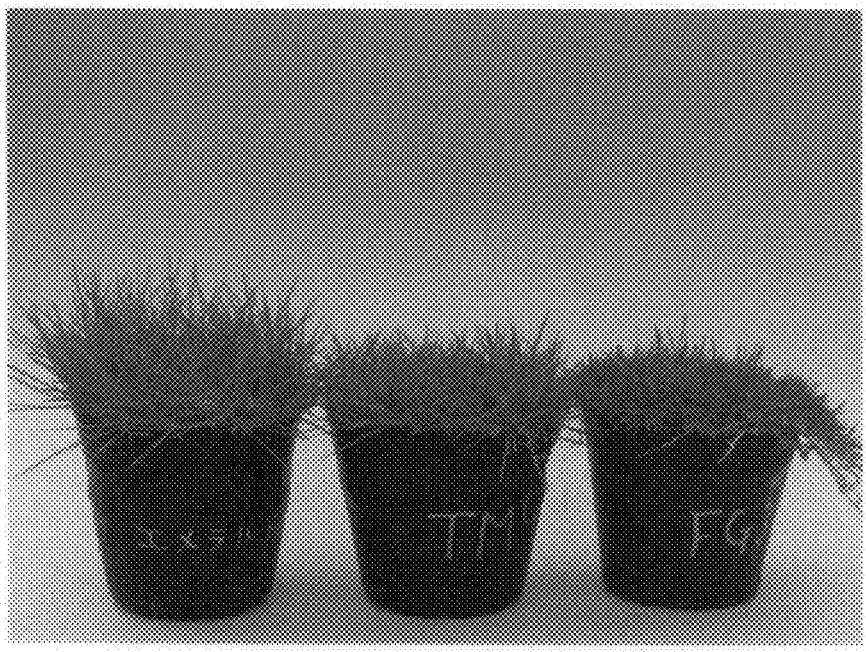
Figure 8:
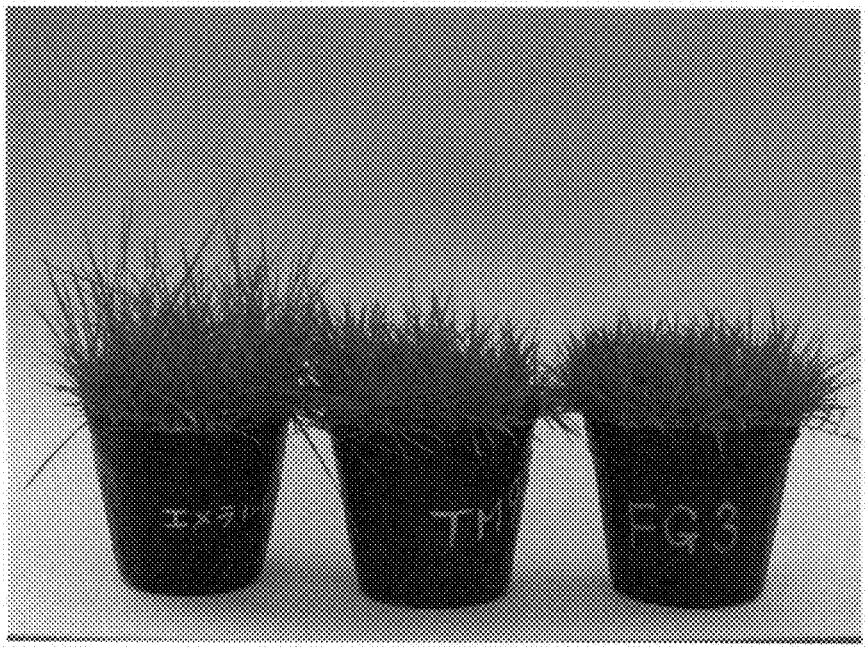

FIG. 8 is a set of photographs comparing grass shapes after culture in a shade tolerance test (Panel (1): untreated plots; Panel (2): light shielding plots) (Left: Emerald; Middle: TM9; Right: 'TMX' in Panels (1) and (2)). Photographed on Sep. 7, 2006 in Nishikamo-gun, Aichi, Japan.

DETAILED BOTANICAL DESCRIPTION OF THE PLANT

1. Characteristics of the plant body of the present invention

1) Overview

Self-fertile seeds (50,000 seeds) of a lawn cultivar 'TM9' (*Zoysia matrella* Merr.) were seeded (June 2003), 70 individuals exhibiting short plant height as pot seedlings were selected from the germinated individuals (in the year 2003), and 6 individuals were selected from among these seedlings based on their growing properties as a pot seedling (in the year 2004). They were planted in a field and an outdoor cultivation test was initiated (in the year 2005). The present cultivar was obtained after completion of cultivation tests in various locations throughout Japan (completed in the year 2006). Characteristics of the present cultivar are as follows: extremely creeping plant form; spikestem of medium-sized thickness and short length; dense stolons of medium-sized thickness; leaves of very short length, very narrow leaf width, and a yellowish green leaf color; short spike length and grayed purple spike color; medium spikelet length, narrow spikelet width, and a small number of spikelets; moderate initial growth; moderate plant vigor in spring and good plant vigor in fall; medium (not early nor late) timing in spike-sprouting; spike-sprouting only in spring with a medium number of spikes; medium (not early nor late) timing in turning green; medium (not early nor late) timing in turning red; medium winter hardiness; good summer tolerance; strong shade tolerance; medium drought tolerance; medium salinity tolerance; and medium tread pressure resistance.

2) Comparison with control cultivars (Table 1)

TABLE 1

| | Item | Trait | Present cultivar 'TMX' |
|---|---|---|---|
| 1 | Height | Height of mature plant | Low (2.0 cm) |
| 2 | Plant | Plant | Extremely creeping |
| 3 | Stem | Thickness of spikestem | Medium (0.7 mm) |
| | | Length of spikestem | Short (2 cm) |
| 4 | Stolon | Density of stolons | Dense |
| | | Internode length of stolon | 18 mm |
| | | Thickness of stolon | Medium (1.0 mm) |
| 5 | Foliage | Leaf length | Extremely short (1 cm) |
| | | Leaf width | Extremely narrow (1.2 mm) |
| | | Leaf color (Whole leaf including both sides, apex and margin) | 141C: Strong yellowish green group |
| 6 | Spike | Spike length | Short (12 mm) |
| | | Spike color | 183A: Grayed purple group |
| | | Spike diameter | 2 mm |
| | | Spikelet length | Medium (2.7 mm) |
| | | Spikelet width | Narrow (0.8 mm) |
| | | Number of spikelet | Few (17) |
| 7 | Initial growth | Initial growth | Medium |
| 8 | Plant vigor | Plant vigor in spring | Moderate |
| | | Plant vigor in fall | Good |
| 9 | Spike-sprouting time | Beginning of spike-sprouting | Medium (not early nor late) |
| 10 | Spike-sprouting properties | Spike-sprouting in spring/fall | Spike-sprouting only in spring |
| | | Number of spikes | Medium (100-150 spike/m$^2$) |
| 11 | Growing period | Timing to turn green | Medium (not early nor late) |
| | | Timing to turn red | Medium (not early nor late) |
| 12 | Winter hardiness | Good/Bad in winter hardiness | Medium |
| 13 | Summer tolerance | Good/Bad in summer tolerance | Good |
| 14 | Environmental tolerance | Shade tolerance | Strong |
| | | Drought tolerance | Medium |
| | | Salinity tolerance | Medium |
| 15 | Tread pressure resistance | Tread pressure resistance | Medium |

| | Item | Trait | Control cultivar 'Emerald' | Control cultivar 'TM9' |
|---|---|---|---|---|
| 1 | Height | Height of mature plant | High (14.0 cm) | Middle (5.7 cm) |
| 2 | Plant | Plant | Intermediate | Creeping |
| 3 | Stem | Thickness of spikestem | Medium (0.7 mm) | Medium (0.7 mm) |
| | | Length of spikestem | Medium (5 cm) | Short (2 cm) |
| 4 | Stolon | Density of stolons | Dense | Extremely dense |
| | | Internode length of stolon | 22 mm | 19 mm |
| | | Thickness of stolon | Medium (1.1 mm) | Medium (1.1 mm) |
| 5 | Foliage | Leaf length | Short (8 cm) | Extremely short to short (4 cm) |
| | | Leaf width | Narrow (1.6 mm) | Narrow (1.8 mm) |
| | | Leaf color (Whole leaf including both sides, apex and margin) | 144A: Yellow green group | 137A: green group |
| 6 | Spike | Spike length | Short (17 mm) | Short (14 mm) |
| | | Spike color | 183A: Grayed purple group | 183A: Grayed purple group |
| | | Spike diameter | 2 mm | 2 mm |
| | | Spikelet length | Medium (3.2 mm) | Medium (2.8 mm) |
| | | Spikelet width | Medium (1.2 mm) | Medium (1.1 mm) |
| | | Number of spikelet | Few (16) | Few (17) |
| 7 | Initial growth | Initial growth | Medium | Medium |
| 8 | Plant vigor | Plant vigor in spring | Moderate | Moderate |
| | | Plant vigor in fall | Good | Good |
| 9 | Spike-sprouting time | Beginning of spike-sprouting | Medium (not early nor late) | Medium (not early nor late) |
| 10 | Spike-sprouting properties | Spike-sprouting in spring/fall | Spike-sprouting only in spring | Spike-sprouting only in spring |
| | | Number of spikes | Medium (100-150 spike/m$^2$) | Many (150-200 spike/m$^2$) |

TABLE 1-continued

| | | | | |
|---|---|---|---|---|
| 11 | Growing period | Timing to turn green | Medium (not early nor late) | Medium (not early nor late) |
| | | Timing to turn red | Medium (not early nor late) | Medium (not early nor late) |
| 12 | Winter hardiness | Good/Bad in winter hardiness | Medium | Medium |
| 13 | Summer tolerance | Good/Bad in summer tolerance | Good | Good |
| 14 | Environmental tolerance | Shade tolerance | Medium | Medium |
| | | Drought tolerance | Medium | Medium |
| | | Salinity tolerance | Medium | Medium |
| 15 | Tread pressure resistance | Tread pressure resistance | Medium | Medium |

Colors are based on the RHS color chart.

3) Other characteristics of the plant body of the present invention

*Length of internode.*—18 mm.

*Diameter of internode.*—1.0 mm.

*Blade villus.*—Hairs absent on adaxial and abaxial leaf surface.

*Ligule hair.*—0.1 mm in length, continuously.

*Color of anther.*—183D grayed purple group.

*Color of stigma.*—8C reverse yellow group.

*Average number of florets per raceme.*—17.

*Total length of culm up to the node immediately below the flag leaf (including the flower portion).*—1.4 cm.

*Length of stalk of inflorescence.*—0.7 cm.

*Length of flower portion.*—1.2 cm.

*Color of mature spikelet.*—161D grayed yellow green group.

*Color of stolon.*—60B red purple group and 144D yellow group.

4) Sensitivity to diseases or insect pests 'TMX' did not exhibit sensitivity to diseases or insect pests that are generally found in plants of the *Zoysia* genus over 21 months starting from April in 2005 in Japan.

*Notes:

*Type of plant.*—lawn.

*Name of the applied cultivar.*—'TMX'.

*Cultivator.*—Kunio Matsui.

*Address of the applicant.*—1 Toyota-Cho, Toyota-shi, Aichi, Japan.

*Cultivation site.*—Nishikamo-gun, Toyota-shi, Aichi, Japan (Latitude:N 35° 08' 06"; Longitude: E 137° 05' 59").

*Place where characteristics research was conducted.*—Nishikamo-gun, Toyota-shi, Aichi, Japan (Latitude: N 35° 08' 06"; Longitude: E 137° 05' 59").

*Name of researcher who conducted characteristics research.*—Kunio Matsui.

*Period when characteristics research was conducted.*—2005-2006.

*Control cultivar (most approximate cultivar).*—'TM9'.

5) Characteristics by which the present cultivar is distinguished from the control cultivars a) Control cultivars 'Emerald' 'TM9' b) Distinguishing characteristics

The present cultivar can be distinguished from 'Emerald' in that the present cultivar has a low height (2.0 cm) (whereas 'Emerald' has a high height (14.0 cm)); an extremely creeping plant form (whereas 'Emerald' has an intermediate plant form); short-length spikestems (2 cm) (whereas 'Emerald' has medium-length spikestems (5 cm)); very short leaves (1 cm) (whereas 'Emerald' has short leaves (8 cm)); an extremely narrow leaf width (1.2 mm) (whereas 'Emerald' has a narrow leaf width (1.6 mm)); a strong yellowish green leaf color (141C) (whereas 'Emerald' has a yellow green leaf color (144A)); a narrow spikelet width (0.8 mm) (whereas 'Emerald' has a medium spikelet width (1.2 mm)); and a strong shade tolerance (whereas 'Emerald' has a medium shade tolerance).

The present cultivar can be distinguished from 'TM9' in that the present cultivar has a low height (2.0 cm) (whereas 'TM9' has a medium height (5.7 cm)); an extremely creeping plant form (whereas 'TM9' has a creeping plant form); dense stolons (whereas 'TM9' has extremely dense stolons); very short leaves (1 cm) (whereas 'TM9' has short to extremely short leaves (4 cm)); an extremely narrow leaf width (1.2 mm) (whereas 'TM9' has a narrow leaf width (1.8 mm)); a strong yellowish green leaf color (141C) (whereas 'TM9' has a green leaf color (137A)); a narrow spikelet width (0.8 mm) (whereas 'TM9' has a medium spikelet width (1.1 mm)); a medium number of spikes (whereas 'TM9' has a large number of spikes); and a strong shade tolerance (whereas 'TM9' has a moderate shade tolerance).

6) Cultivation conditions for characteristic research experiment of above 1) to 5)

*a Cultivation site.*—Nishikamo-gun, Aichi, Japan (Latitude: N 35° 08' 06"; Longitude: E 137° 05' 59").

*b Cultivation time and period.*—21 months from April, 2005.

*c Cultivation method.*—(Examples: cultivation style such as on bare ground, in a facility, field planting or pot planting, cultivation scale, etc.).

Pot seedlings reproduced by cutting rootstocks and stolons and planting them in soil were raised in greenhouse for two months and fix planted on bare ground in April along with control cultivars in order to perform a characteristic research experiment. Five individuals (triplicates) were fix planted at a density of one seedling per an area of 200 cm × 200 cm in an individually planted plot while they were fix planted in triplicates at a density of one seedling per an area of 15 cm × 15 cm in a dense plated test plot having an area of 150 cm × 150 cm thereby performing a characteristic research experiment.

7) Shade tolerance test

Figure 1:
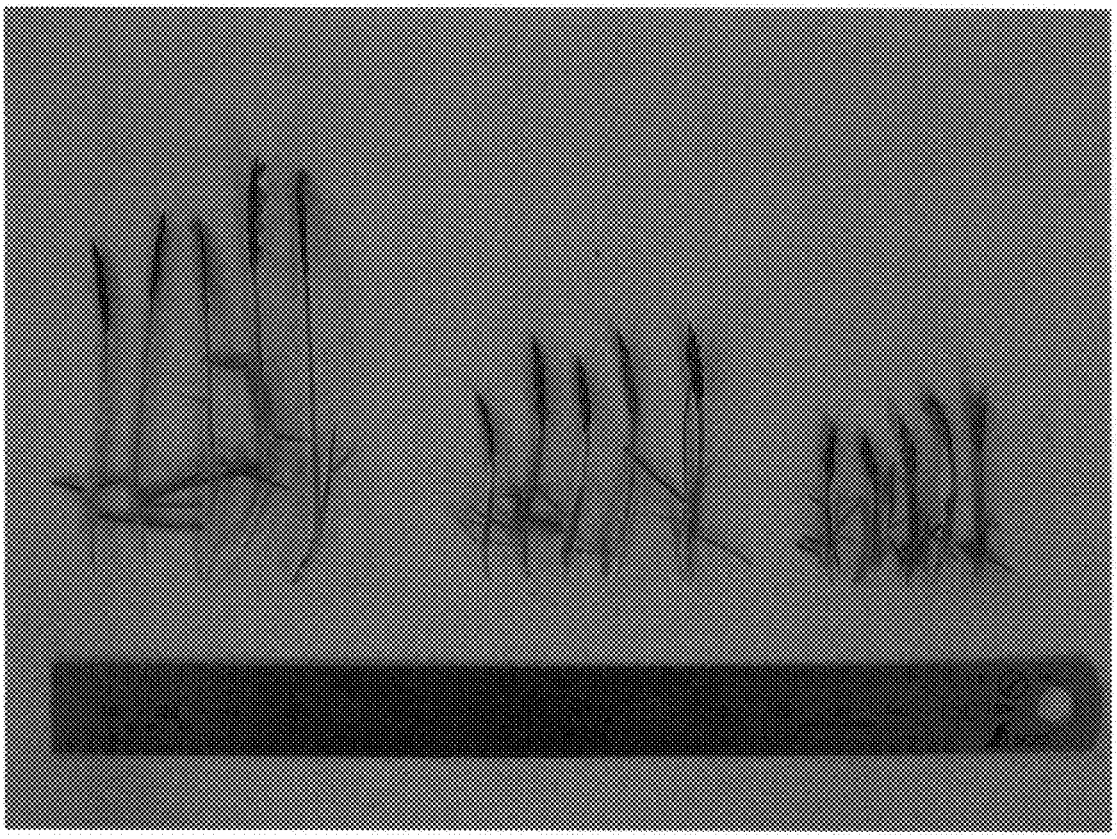
Figure 2:
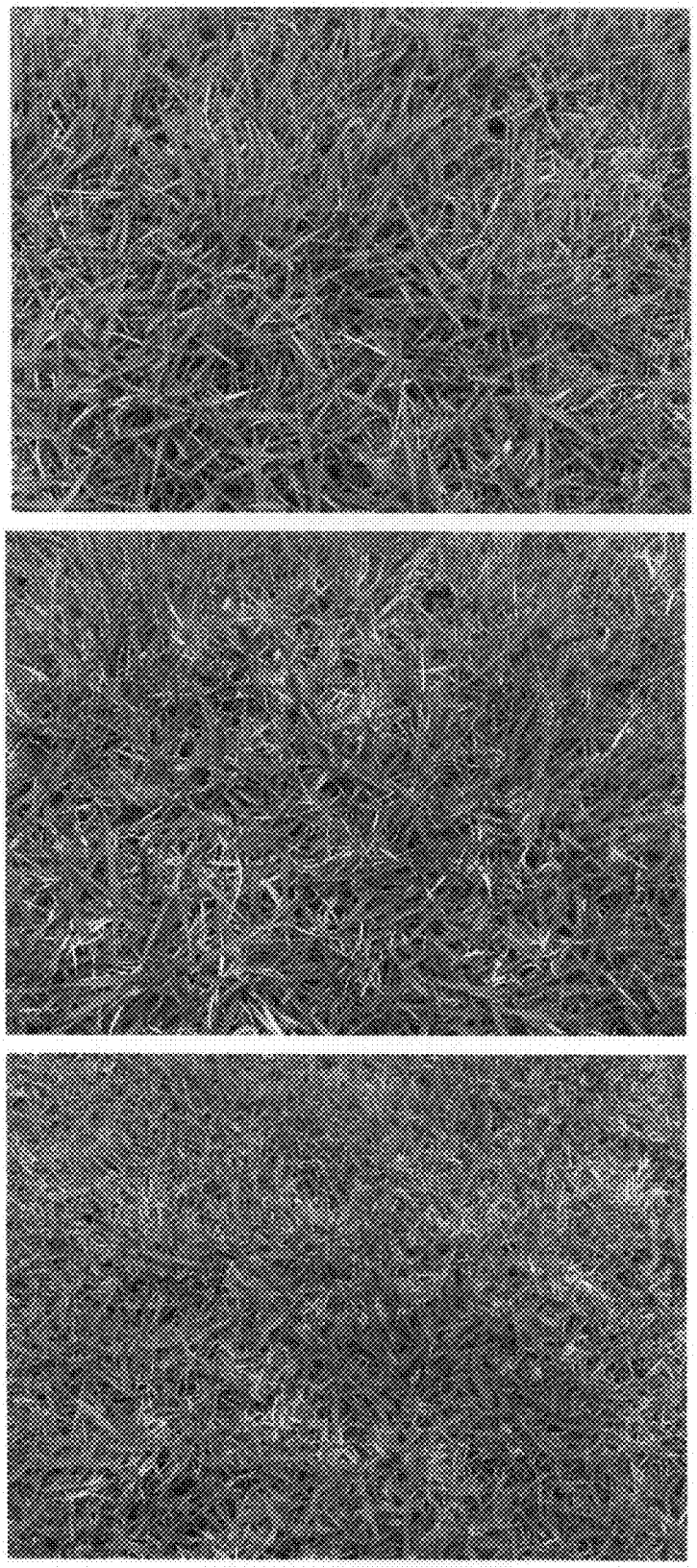
Figure 3:
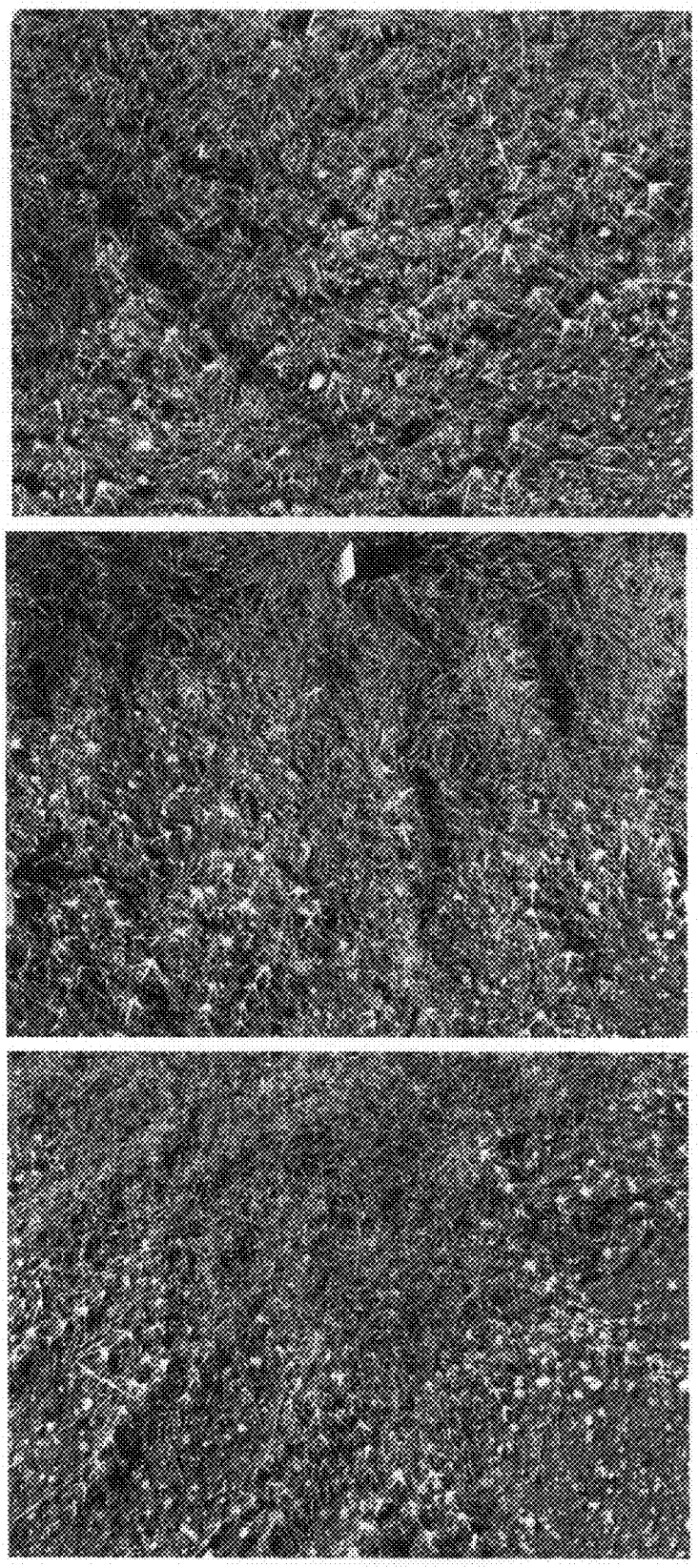
Figure 4:
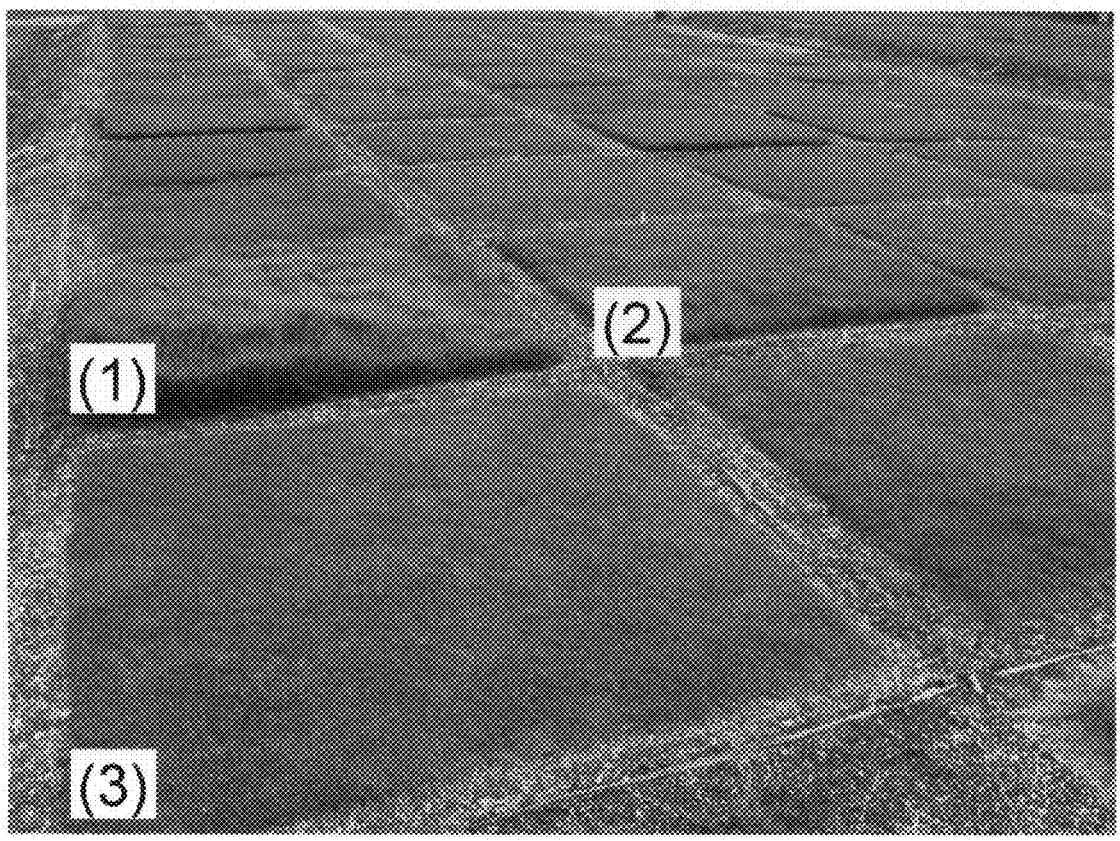
Figure 5:
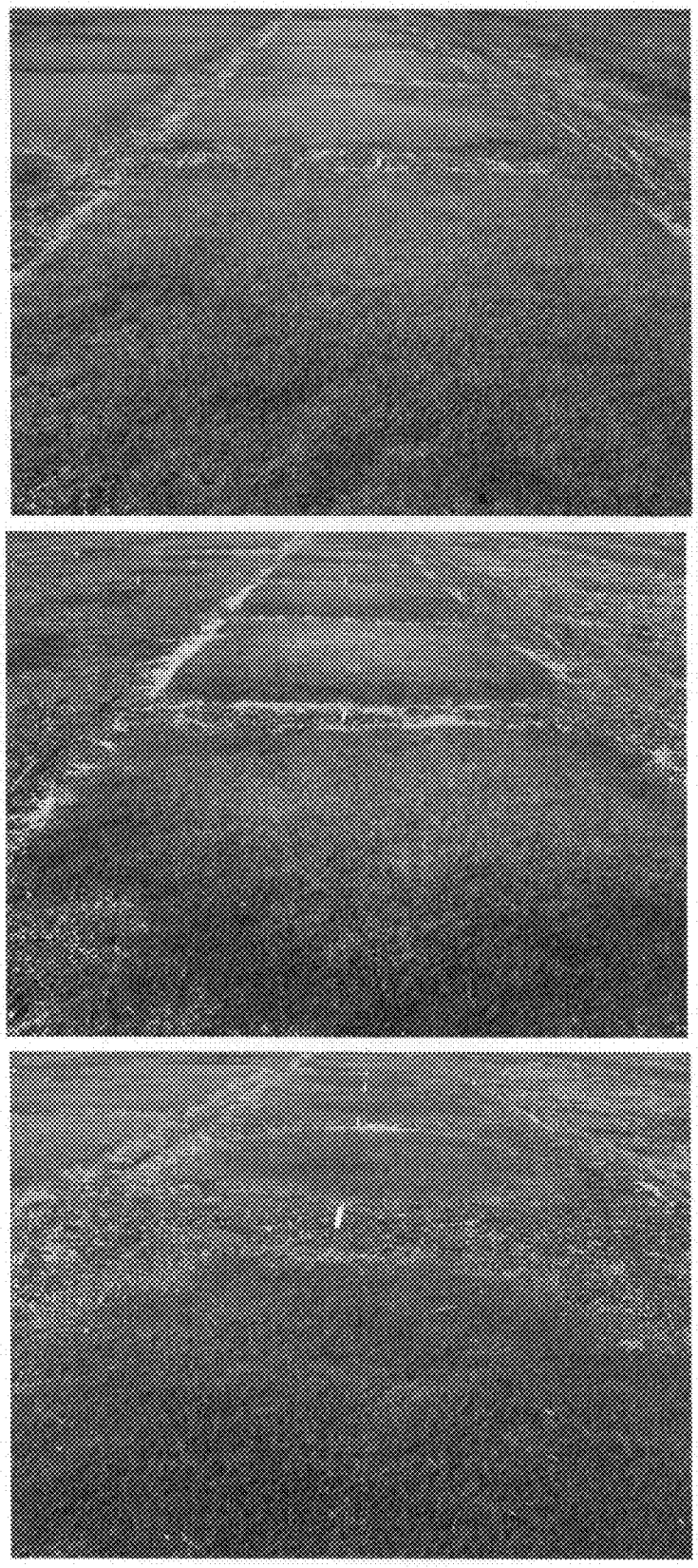
Figure 6:
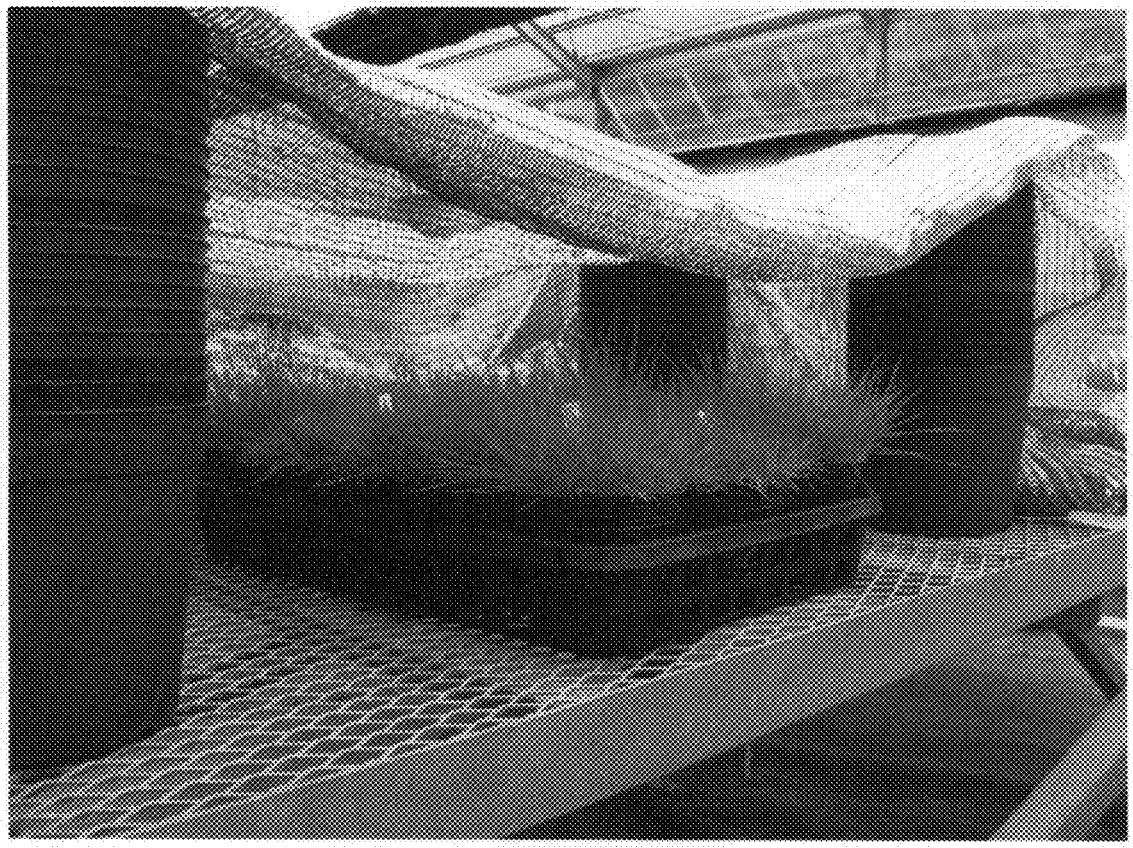
FIG. 6 is a photograph showing culture of control cultivars and the present cultivar ('TMX') in a shade tolerance test with the use of a light-shading net. Photographed on Sep. 7, 2006 in Nishikamo-gun, Aichi, Japan.
Figure 7:
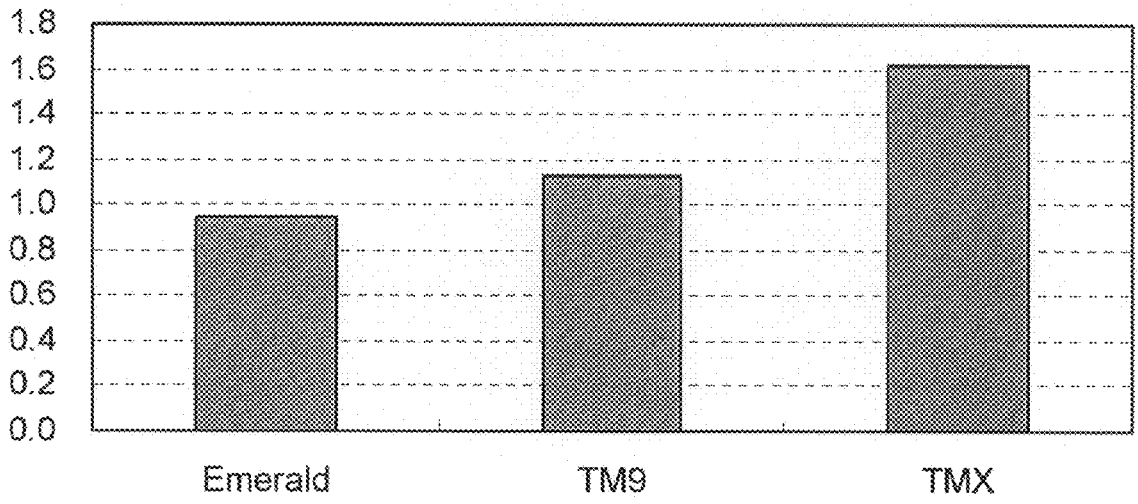
FIG. 7 is a graph showing the relative amounts of growth with 75% light shielding in a shade tolerance test (light shielding/untreated plots).

*a) Test method.*—Three pot seedlings (pot diameter: 12 cm) of each of 'Emerald', 'TM9', and 'TMX' were raised under 75% light shielding with a light-shading net for approximately 2 months from July 6 to September 7 in 2007 in Nishikamo-gun, Aichi, Japan (Latitude: N 35° 08' 06"; Longitude: E 137° 05' 59") (FIG. 6). In addition, three pot seedlings of each of the above cultivars were raised under conditions without the use of a light-shielding net (untreated plot). The aerial portions of each cultivar were mowed. Then, the mean value of the weights of the mowed parts of three pot seedlings that had been raised while covered with a light-shading net was divided by a mean value of the weights of the mowed parts of three pot seedlings in the untreated plot. Thus, the relative amount of growth was calculated.

b) *Results.*—The seedlings of 'Emerald' and 'TM9' that had been raised with light shielding grew to an extent comparable to that of those in the untreated plot. Meanwhile, the amount of growth of the seedlings of 'TMX' that had been raised with light shielding was approximately 1.6 times greater than that of those in the untreated plot (FIG. 7). In addition, the leaf length became longer in the case of every cultivar raised with light shielding. However, no abnormalities in leaves or the like were found (FIG. 8).

Accordingly, the shade tolerance of 'TMX' was likely to be stronger than that of 'Emerald' and of 'TM9'.

2. Reproduction method

*Vegetative propagation.*—Rootstocks, stolons, tillers, and turf.

3. Conditions of keeping and storage the plant having identifiable characteristics

*Place where the plant is maintained and/or stored.*—Nishikamo-gun, Aichi, Japan (Latitude: N 35° 08' 06"; Longitude: E 137° 05' 59").

*Method of maintenance/storage.*—pot planting and ground planting.

4. History of cultivating the present cultivar

1) *Material of new cultivar.*—Self-fertile seed of 'TM9' (*Zoysia matrella* Merr.).

2) *Cultivation site.*—Nishikamo-gun in Aichi, Japan (Latitude: N 35° 08' 06"; Longitude: E 137° 05' 59").

3) *History of cultivating the cultivar.*

Self-fertile seeds of 'TM9' were seeded in June, 2003, and individuals exhibiting short plant height as pot seedlings were selected from the germinated individuals. The thus selected lines were reproduced by root separation asexually in April 2004 and the uniformity of these vegetative propagated lines was respectively confirmed in greenhouse by January, 2005. Newly root separated lines (January 2005) were fix planted in a field in April 2005. A line exhibiting a short leaf length and a satisfactory initial growth was selected and the stability thereof was confirmed to complete the cultivating of the new cultivar on Dec. 28, 2006. All cultivating was done at the above-noted cultivation site.

5. Main use of the present cultivar The present cultivar can be used for ground covering of a park, garden, etc.

6. Other items in relation to the cultivation of the present cultivar

1) *Applicable area.*—Warm area.

2) *Specific cultivation site in Japan Address* (*Zip code.* 470-0201).—1099 Kurozasa-Marune, Miyoshi-machi, Nishikamo-gun, Aichi, Japan (Latitude: N 35°08' 06"; Longitude: E 137° 05' 59")

3) Cultivation style: Normal cultivation. Bare ground. Seasons suitable for seeding, planting, etc.

*Other reproduction method.*—Vegetative propagation by stolons from the beginning of April to the beginning of May/year round Blooming season, harvest season, and any other seasons in cultivation stage suitable for specifying characteristics of the present cultivar.

*Blooming season.*—from the beginning to the end of May /year round.

*Greening season.*—from the end of April to the end of October/year round.

4) Other items to be mentioned for the cultivation of the present cultivar

The present cultivar is extremely creeping in plant form and short in leaf length, which allows weeds readily to grow. Frequent weeding is therefore required.

7. Other Information

When the present cultivar is allowed freely to grow, the plant height (i.e. the height from the ground to the tip of the leaf blade) is as about ¼ of that of 'Emerald' and half of that of 'TM9'.

The variety 'TMX' produces seeds, but is not propagated by seed. The number of seed per plant, seed length, seed width and generic color of seed correspond to the number of spikelets, spikelet length, spikelet width and spike color, respectively.

What is claimed is:

1. A new and distinctive variety of *Zoysia matrella* Merr. plant named 'TMX' as illustrated and described in the present specification.

* * * * *

(1)

(2)

UNITED STATES PATENT AND TRADEMARK OFFICE

CERTIFICATE OF CORRECTION

PATENT NO. : PP21,426 P3
APPLICATION NO. : 12/149800
DATED : October 26, 2010
INVENTOR(S) : Kunio Matsui It is certified that error appears in the above-identified patent and that said Letters Patent is hereby corrected as shown below:

On the title page, Item (73), the address of the Assignee is incorrect. Item (73) should read:

-- (73) Assignee: Toyota Jidosha Kabushiki Kaisha, Toyota-shi (JP)--

Signed and Sealed this
Fifth Day of April, 2011

David J. Kappos

David J. Kappos
*Director of the United States Patent and Trademark Office*